US009750646B2

(12) United States Patent
Varga et al.

(10) Patent No.: US 9,750,646 B2
(45) Date of Patent: Sep. 5, 2017

(54) SYSTEMS AND METHODS FOR MONITORING AND CONTROLLING AN ABSORBENT ARTICLE CONVERTING LINE

(71) Applicant: The Procter & Gamble Company, Cincinnati, OH (US)

(72) Inventors: Stephen Michael Varga, Loveland, OH (US); Bradley Edward Walsh, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 53 days.

(21) Appl. No.: 14/745,530

(22) Filed: Jun. 22, 2015

(65) Prior Publication Data

US 2015/0374557 A1    Dec. 31, 2015

Related U.S. Application Data

(60) Provisional application No. 62/017,292, filed on Jun. 26, 2014.

(51) Int. Cl.
*G06K 9/00* (2006.01)
*A61F 13/15* (2006.01)
(Continued)

(52) U.S. Cl.
CPC .... *A61F 13/15772* (2013.01); *G02B 13/0025* (2013.01); *G06T 7/0004* (2013.01);
(Continued)

(58) Field of Classification Search
None
See application file for complete search history.

(56) References Cited

U.S. PATENT DOCUMENTS 4,519,041 A * 5/1985 Fant et al. ............. G01N 21/89
382/108
4,974,077 A * 11/1990 Kusaba ................. G01B 11/028
382/141

(Continued)

FOREIGN PATENT DOCUMENTS

EP    1 528 907 B1    9/2008

OTHER PUBLICATIONS

PCT International Search Report dated Sep. 7, 2015, 10 pages.

*Primary Examiner* — Avinash Yentrapati
(74) *Attorney, Agent, or Firm* — Charles R. Matson

(57) ABSTRACT

The present disclosure relates to methods and apparatuses for monitoring substrates advancing along a converting apparatus in a machine direction. The apparatus may include an analyzer connected with a line scan camera through a communication network. The analyzer may be configured as a field programmable gate array, an application specific integrated circuit, or a graphical processing unit. In addition, the line scan camera may include a linear array of pixel data and define a linear field of view, wherein the line scan camera is arranged such that the linear field of view extends in the machine direction. The apparatus may further include an illumination source that illuminates the linear field of view. In operation, the substrate is advanced in the machine direction such that a portion of the substrate advances through the linear field of view. In turn, the apparatus may be configured to perform various monitoring and/or control functions.

23 Claims, 15 Drawing Sheets

(51) Int. Cl.
  *G02B 13/00* (2006.01)
  *G06T 7/00* (2017.01)
  *H04N 5/225* (2006.01)
  *H04N 5/247* (2006.01)
  *G06T 7/73* (2017.01)
  *G06T 7/13* (2017.01)
  *G06T 7/292* (2017.01)

(52) U.S. Cl.
  CPC ............... *G06T 7/13* (2017.01); *G06T 7/292* (2017.01); *G06T 7/73* (2017.01); *G06T 7/97* (2017.01); *H04N 5/2256* (2013.01); *H04N 5/247* (2013.01); *A61F 2013/1578* (2013.01); *A61F 2013/15788* (2013.01); *A61F 2013/15796* (2013.01); *G06T 2207/10024* (2013.01); *G06T 2207/30124* (2013.01)

(56) References Cited

U.S. PATENT DOCUMENTS

| | | | |
|---|---|---|---|
| 5,286,543 A | 2/1994 | Ungpiyakul et al. | |
| 5,359,525 A | 10/1994 | Weyenberg | |
| 5,555,315 A * | 9/1996 | Itakura | G01N 21/95692 348/131 |
| 6,801,828 B2 | 10/2004 | Chapple et al. | |
| 6,820,022 B2 | 11/2004 | Carbone et al. | |
| 7,123,981 B2 | 10/2006 | Dollevoet et al. | |
| 8,145,343 B2 | 3/2012 | DeBruler et al. | |
| 8,145,344 B2 | 3/2012 | DeBruler et al. | |
| 8,244,393 B2 | 8/2012 | McLaughlin et al. | |
| 8,279,491 B2 * | 10/2012 | Ishibashi | B41J 2/2135 347/107 |
| 2003/0169433 A1 * | 9/2003 | Koele et al. | A61F 13/15772 356/614 |
| 2004/0030435 A1 * | 2/2004 | Popp et al. | A61F 13/15772 700/110 |
| 2004/0064324 A1 * | 4/2004 | Graumann | G10L 21/038 704/500 |
| 2004/0118892 A1 | 6/2004 | Weber et al. | |
| 2004/0151356 A1 * | 8/2004 | Li et al. | G06K 9/527 382/131 |
| 2006/0017676 A1 * | 1/2006 | Bowers et al. | G01N 21/278 345/87 |
| 2007/0058840 A1 * | 3/2007 | Singh et al. | A61F 13/15772 382/111 |
| 2007/0142798 A1 | 6/2007 | Goodlander et al. | |
| 2007/0142806 A1 | 6/2007 | Roe et al. | |
| 2007/0287983 A1 | 12/2007 | Lodge et al. | |
| 2008/0132865 A1 * | 6/2008 | Li et al. | A61F 13/15 604/378 |
| 2011/0141269 A1 * | 6/2011 | Varga et al. | G01N 21/8903 348/92 |
| 2011/0247199 A1 * | 10/2011 | Lavon et al. | A61F 13/15585 29/650 |
| 2013/0317637 A1 * | 11/2013 | Singh et al. | G05B 17/02 700/97 |
| 2014/0169632 A1 * | 6/2014 | Ogasawara et al. | A61F 13/15658 382/103 |
| 2015/0374557 A1 * | 12/2015 | Varga et al. | A61F 13/15772 382/103 |

* cited by examiner

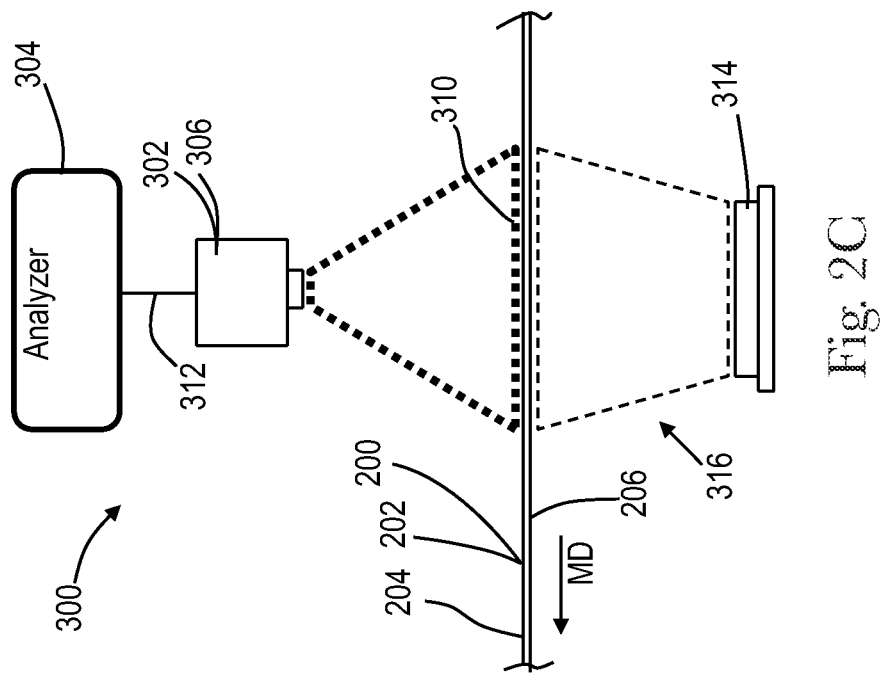
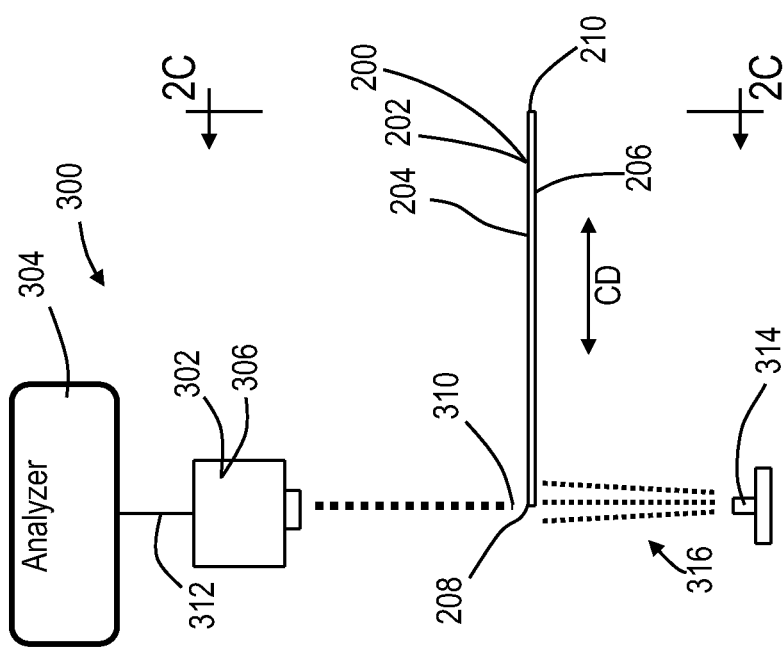

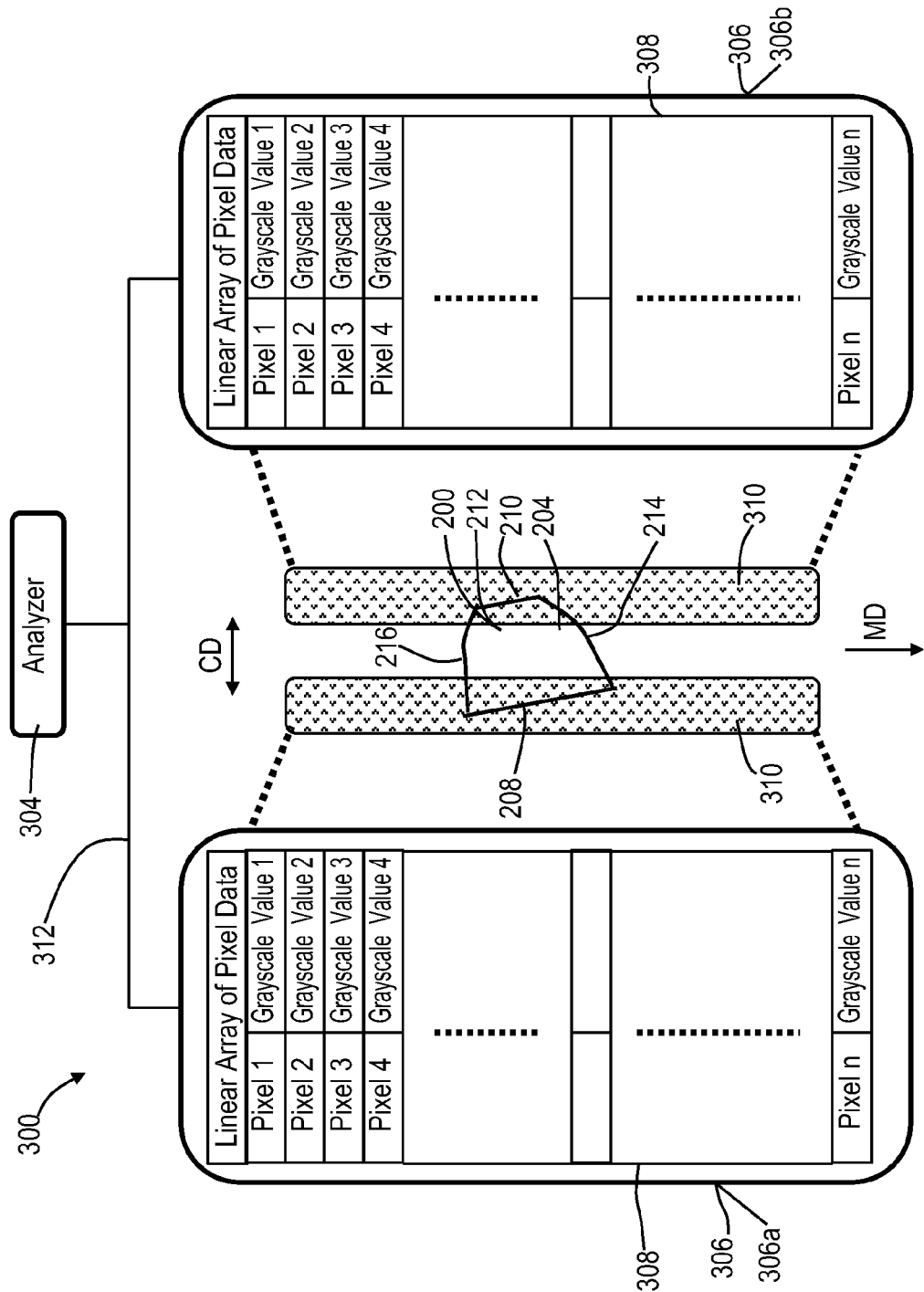

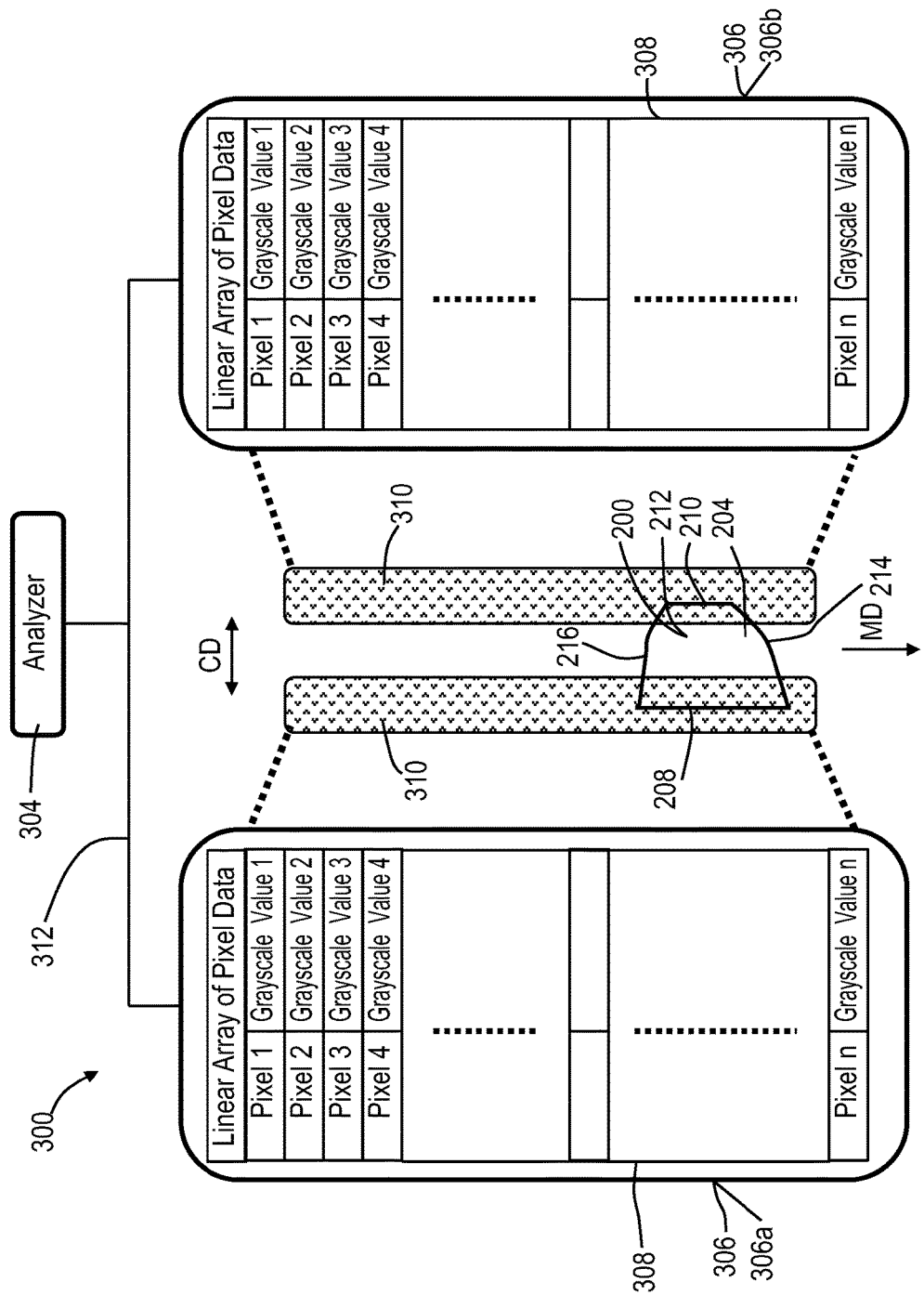

SYSTEMS AND METHODS FOR MONITORING AND CONTROLLING AN ABSORBENT ARTICLE CONVERTING LINE

CROSS REFERENCE TO RELATED APPLICATION

This application claims the benefit of U.S. Provisional Application No. 62/017,292 filed on Jun. 26, 2014, which is incorporated herein by reference.

FIELD OF THE INVENTION

The present disclosure relates to systems and methods for manufacturing disposable absorbent articles, and more particularly, systems and methods for monitoring advancing substrates and/or controlling a converting apparatus with an analyzer receiving feedback from a line scan camera positioned to have a field of view oriented in a machine direction.

BACKGROUND OF THE INVENTION

Along an assembly line, diapers and various types of other absorbent articles may be assembled by adding components to and otherwise modifying an advancing, continuous web of material. For example, in some processes, advancing webs of material are combined with other advancing webs of material. In other examples, individual components created from advancing webs of material are combined with advancing webs of material, which in turn, are then combined with other advancing webs of material. Webs of material and component parts used to manufacture diapers may include: backsheets, topsheets, absorbent cores, front and/or back ears, fastener components, and various types of elastic webs and components such as leg elastics, barrier leg cuff elastics, and waist elastics. Once the desired component parts are assembled, the advancing web(s) and component parts are subjected to a final knife cut to separate the web(s) into discrete diapers or other absorbent articles. The discrete diapers or absorbent articles may also then be folded and packaged.

For purposes of web control and/or monitoring purposes, absorbent article converting lines may utilize various types of sensor technology to detect various types of inspection data relating to the continuous webs and discrete components added to the webs along the converting line as absorbent articles that are constructed therefrom. Example sensor technology may include vision systems, photoelectric sensors, proximity sensors, laser or sonic distance detectors, and the like. Sensor data may be communicated to a controller in various ways. In turn, the controller may be programmed to receive sensor data and report and/or store such data as well as make adjustments to manufacturing processes.

In some manufacturing processes, cameras are arranged adjacent converting lines in order to communicate data to the controller relating to positions and/or orientations of advancing webs and components. Although cameras may detect and communicate valuable data to the controller, the controller may not be able to track the exact locations and speeds of an advancing continuous web and/or component with a very large degree of accuracy due to relatively slow sensor and control loop times. And such slow loop times may be exacerbated at the high speed production rates of some absorbent article processes. Consequently, it would be beneficial to configure and utilize visions systems in combinations with controllers that are able to detect and track the locations and speeds of advancing continuous webs and/or components advancing at relatively high production speeds.

SUMMARY OF THE INVENTION

In one form, a method for manufacturing an absorbent article comprises the steps of: providing a line scan camera comprising a linear array of pixel data and defining a linear field of view; providing an analyzer selected from the group consisting of: a field programmable gate array, an application specific integrated circuit, and graphical processing unit; arranging the line scan camera such that the linear field of view extends in a machine direction; operating an illumination source to define an illumination field that illuminates the linear field of view; providing a substrate comprising a first surface and an opposing second surface, the substrate further comprising a first longitudinal side edge and a second longitudinal side edge separated from the first longitudinal side edge in a cross direction; advancing the substrate in the machine direction such that the first longitudinal side edge travels through the linear field of view; communicating a first set of grayscale values of pixels from the linear array of pixel data from the line scan camera to the analyzer; and determining a first position of the first longitudinal side edge based on the grayscale value of at least one pixel.

In another form, a method for manufacturing an absorbent article comprises the steps of: providing a first line scan camera comprising a linear array of pixel data and defining a first linear field of view; providing a second line scan camera comprising a linear array of pixel data and defining a second linear field of view; providing an analyzer selected from the group consisting of: a field programmable gate array, an application specific integrated circuit, and graphical processing unit; arranging the first and second line scan cameras such that the first and second linear fields of view extend in a machine direction; operating an illumination source to define an illumination field that illuminates the first and second linear fields of view; providing a substrate comprising a discrete component having a width in the cross direction, the substrate further comprising a first lateral side edge and a second lateral side edge separated from the first lateral side edge to define a length in the machine direction; advancing the substrate in the machine direction such that the first and second lateral side edges travel through the first linear field of view, and such that the first and second lateral side edges travel through the second linear field of view; communicating a first set of grayscale values of pixels from the linear array of pixel data from the first and second line scan cameras to the analyzer; and communicating a second set of grayscale values of pixels from the linear array of pixel data from the first and second line scan cameras to the analyzer; and determining an orientation of the substrate relative to the machine direction based on the first and second sets of grayscale values of at least two pixels.

In yet another form, an apparatus for monitoring a substrate comprising a first surface and an opposing second surface, the substrate further comprising a first longitudinal side edge and a second longitudinal side edge separated from the first longitudinal side edge to define a width in a cross direction, the substrate advancing along a converting apparatus in a machine direction and the apparatus comprises: a communication network; an analyzer connected with the communication network, the analyzer comprising a linear array of pixel data and defining a linear field of view extending in the machine direction, wherein the analyzer is selected from the group consisting of: a field programmable gate array, an application specific integrated circuit, and graphical processing unit; a line scan camera connected with the communication network, the line scan camera comprising a linear array of pixel data and defining a linear field of view, wherein the line scan camera is arranged such that the linear field of view extends in the machine direction; an illumination source defining an illumination field that illuminates the linear field of view; and wherein the analyzer is configured to determine a position of the first longitudinal side edge of the substrate based on based on a set of grayscale values of pixels from the linear array of pixel data from the analyzer.

BRIEF DESCRIPTION OF THE DRAWINGS

FIG. 2B is a side view of the inspection system and advancing substrate taken along the sectional line 2B-2B of FIG. 2A.

FIG. 2C is a side view of the inspection system and advancing substrate taken along the sectional line 2C-2C of FIG. 2B.

FIG. 7B is a detailed schematic top side view showing the continued advancement of the substrate from FIG. 7A through the fields of view of the line scan cameras.

FIG. 7C is a detailed schematic top side view showing the continued advancement of the substrate from FIG. 7B through the fields of view of the line scan cameras.

DETAILED DESCRIPTION OF THE INVENTION

Figure 1:
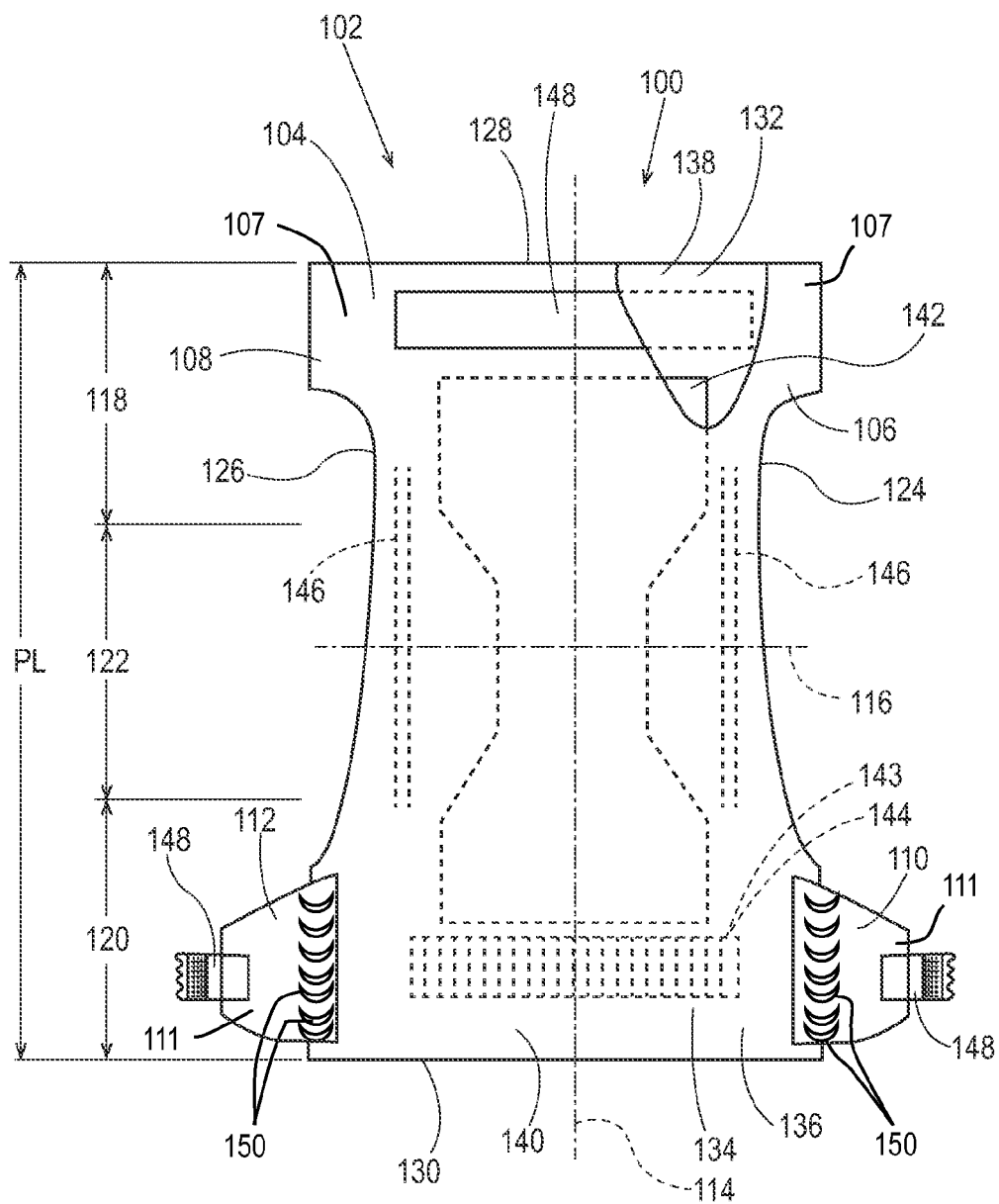
FIG. 1 is a top plan view of a disposable absorbent article that may include one or more substrates monitored and/or controlled in accordance with the present disclosure.

The following term explanations may be useful in understanding the present disclosure: "Absorbent article" is used herein to refer to consumer products whose primary function is to absorb and retain soils and wastes. "Diaper" is used herein to refer to an absorbent article generally worn by infants and incontinent persons about the lower torso. The term "disposable" is used herein to describe absorbent articles which generally are not intended to be laundered or otherwise restored or reused as an absorbent article (e.g., they are intended to be discarded after a single use and may also be configured to be recycled, composted or otherwise disposed of in an environmentally compatible manner).

An "elastic," "elastomer" or "elastomeric" refers to materials exhibiting elastic properties, which include any material that upon application of a force to its relaxed, initial length can stretch or elongate to an elongated length more than 10% greater than its initial length and will substantially recover back to about its initial length upon release of the applied force.

As used herein, the term "joined" encompasses configurations whereby an element is directly secured to another element by affixing the element directly to the other element, and configurations whereby an element is indirectly secured to another element by affixing the element to intermediate member(s) which in turn are affixed to the other element.

"Longitudinal" means a direction running substantially perpendicular from an end edge, such as a waist edge to a longitudinally opposing end edge, or waist edge, of an absorbent article when the article is in a flat out, uncontracted state, or from a waist edge to the bottom of the crotch, i.e. the fold line, in a bi-folded article. Directions within 45 degrees of the longitudinal direction are considered to be "longitudinal." "Lateral" refers to a direction running from a longitudinally extending side edge to a laterally opposing longitudinally extending side edge of an article and generally at a right angle to the longitudinal direction. Directions within 45 degrees of the lateral direction are considered to be "lateral."

The term "substrate" is used herein to describe a material which is primarily two-dimensional (i.e. in an XY plane) and whose thickness (in a Z direction) is relatively small (i.e. ¹⁄₁₀ or less) in comparison to its length (in an X direction) and width (in a Y direction). Non-limiting examples of substrates include a web, layer or layers or fibrous materials, nonwovens, films and foils such as polymeric films or metallic foils. These materials may be used alone or may comprise two or more layers laminated together. As such, a web is a substrate.

The term "nonwoven" refers herein to a material made from continuous (long) filaments (fibers) and/or discontinuous (short) filaments (fibers) by processes such as spunbonding, meltblowing, carding, and the like. Nonwovens do not have a defined woven or knitted filament pattern.

The term "machine direction" (MD) is used herein to refer to the direction of material flow through a process. In addition, relative placement and movement of material can be described as flowing in the machine direction through a process from upstream in the process to downstream in the process.

The term "cross direction" (CD) is used herein to refer to a direction that is generally perpendicular to the machine direction.

The present disclosure relates to methods and apparatuses for monitoring substrates advancing along a converting apparatus in a machine direction. The substrate may include a first surface and an opposing second surface, and a first longitudinal side edge and a second longitudinal side edge separated from the first longitudinal side edge in a cross direction. The apparatus may include an analyzer connected with a line scan camera through a communication network. In some embodiments, the apparatus may include a cylindrical lens adapted to expand the linear field of view in a cross direction. The analyzer may be configured as a field programmable gate array, an application specific integrated circuit, or a graphical processing unit. In addition, the line scan camera may include a linear array of pixel data and may define a linear field of view, wherein the line scan camera is arranged such that the linear field of view extends in the machine direction. The apparatus may further include an illumination source that illuminates the linear field of view. In operation, the substrate is advanced in the machine direction such that the first longitudinal side edge travels through the linear field of view. In turn, the apparatus may be configured to perform various monitoring and/or control functions. For example, the analyzer may be configured to determine a position of the first longitudinal side edge of the substrate based on based on a set of grayscale values of pixels from the linear array of pixel data from the analyzer.

Arranging a line scan camera in an orientation opposite for which the camera is designed provides a set of image data whereby an x-axis, normally representing a cross direction CD spatial dimension, instead represents a view of a machine direction MD position, and whereby a y-axis, normally representing the machine direction MD, instead becomes a temporal axis. The resulting image data provides a high fidelity position versus time array, which can be updated at a rate enabling very high speed feedback control. The addition of a high speed analyzer, such as an FPGA, ASIC, or GPU, which do not rely on an operating system, enables parallel processing of a large number of position points read from the position versus time array. The deterministic clock of the FPGA or ASIC further benefits the method by providing a low jitter and low latency platform for highly precise closed-loop feedback control. The ease of configuration of the FPGA may further benefit the method by allowing the system to be updated relatively inexpensively and quickly to accommodate variations in substrates or components to be controlled, such as in electro-mechanical to electro-static to pneumatic control loops, as disclosed in U.S. Patent Application entitled, "Method and Apparatus for Transferring a Discrete Substrate," filed on Jun. 26, 2014, 62,017,293.

As discussed in more detail below, the apparatus may be configured with more than one line scan camera having a field of view oriented in the machine direction. For example, the substrate may be continuous or may be in the form of a discrete component. Thus, when in the form of discrete component, the substrate may also include a first lateral side edge and a second lateral side edge separated from the first lateral side edge to define a length in the machine direction. As such, the apparatus may be configured with a first line scan camera comprising a linear array of pixel data and defining a first linear field of view and a second line scan camera comprising a linear array of pixel data and defining a second linear field of view. In turn, the first and second line scan cameras may be arranged such that the first and second linear fields of view extend in a machine direction. In operation, the substrate is advanced in the machine direction such that the first and second lateral side edges travel through the first linear field of view, and such that the first and second lateral side edges travel through the second linear field of view. In turn, a first set of grayscale values of pixels from the linear array of pixel data are communicated from the first and second line scan cameras to the analyzer, and a second set of grayscale values of pixels from the linear array of pixel data are communicated from the first and second line scan cameras to the analyzer 304. Thus, the analyzer may determine an orientation of the substrate relative to the machine direction based on the first and second sets of grayscale values of at least two pixels.

It is to be appreciated that although the methods and apparatuses herein may be utilized in the manufacture of various types of products, the methods and apparatuses herein are discussed below in the context of manufacturing absorbent articles. And more particularly, the methods and apparatuses are discussed in the context of manufacturing diapers. For the purposes of a specific illustration, FIG. 1 shows one example of a disposable absorbent article 100, such as described in U.S. Patent Publication Nos. 2008/0132865 A1 and 2011/0247199 A1, in the form of a diaper 102 that may be constructed from substrates and components monitored and/or controlled during manufacture according to the systems and methods disclosed herein. In particular, FIG. 1 is a plan view of one embodiment of a diaper 102 including a chassis 104 shown in a flat, unfolded condition, with the portion of the diaper 102 that faces away from the wearer oriented towards the viewer. A portion of the chassis structure is cut-away in FIG. 1 to more clearly show the construction of and various features that may be included in embodiments of the diaper.

As shown in FIG. 1, the diaper 102 includes a chassis 104 having a first ear 106, a second ear 108, a third ear 110, and a fourth ear 112. The first ear 106 and second ear 108 may also be referred to herein as front ears 107. And the third ear 110 and the fourth ear 112 may be referred to as back ears 111. The back ears 111 may be connected with the chassis 104 with pressure bonds 150 such as shown for example in FIG. 1. To provide a frame of reference for the present discussion, the chassis 104 is shown with a longitudinal axis 114 and a lateral axis 116. The chassis 104 is shown as having a first waist region 118, a second waist region 120, and a crotch region 122 disposed intermediate the first and second waist regions. In some configurations, the first waist region 118 may correspond with a front waist region, and the second waist region 120 may correspond with a rear waist region. The periphery of the diaper is defined by a pair of longitudinally extending side edges 124, 126; a first outer edge 128 extending laterally adjacent the first waist region 118; and a second outer edge 130 extending laterally adjacent the second waist region 120. As shown in FIG. 1, the chassis 104 includes an inner, body-facing surface 132, and an outer, garment-facing surface 134. A portion of the chassis structure is cut-away in FIG. 1 to more clearly show the construction of and various features that may be included in the diaper. As shown in FIG. 1, the chassis 104 of the diaper 102 may include an outer covering layer 136 including a topsheet 138 and a backsheet 140. An absorbent core 142 may be disposed between a portion of the topsheet 138 and the backsheet 140. As discussed in more detail below, any one or more of the regions may be stretchable and may include an elastomeric material or laminate as described herein. As such, the diaper 102 may be configured to adapt to a specific wearer's anatomy upon application and to maintain coordination with the wearer's anatomy during wear.

The absorbent article may also include an elastic waist feature 143 shown in FIG. 1 in the form of a waist band 144 and may provide improved fit and waste containment. The elastic waist feature 143 may be configured to elastically expand and contract to dynamically fit the wearer's waist. The elastic waist feature 143 can be incorporated into the diaper and may extend at least longitudinally outwardly from the absorbent core 142 and generally form at least a portion of the first and/or second outer edges 128, 130 of the diaper 102. In addition, the elastic waist feature may extend laterally to include the ears. While the elastic waist feature 143 or any constituent elements thereof may comprise one or more separate elements affixed to the diaper, the elastic waist feature may be constructed as an extension of other elements of the diaper, such as the backsheet 140, the topsheet 138, or both the backsheet and the topsheet. In addition, the elastic waist feature 143 may be disposed on the outer, garment-facing surface 134 of the chassis 104; the inner, body-facing surface 132; or between the inner and outer facing surfaces. The elastic waist feature 143 may be constructed in a number of different configurations including those described in U.S. Patent Publication Nos. 2007/0142806A1; 2007/0142798A1; and 2007/0287983A1, all of which are hereby incorporated by reference herein.

As shown in FIG. 1, the diaper 102 may include leg cuffs 146 that may provide improved containment of liquids and other body exudates. In particular, elastic gasketing leg cuffs can provide a sealing effect around the wearer's thighs to prevent leakage. It is to be appreciated that when the diaper is worn, the leg cuffs may be placed in contact with the wearer's thighs, and the extent of that contact and contact pressure may be determined in part by the orientation of diaper on the body of the wearer. The leg cuffs 146 may be disposed in various ways on the diaper 102.

The diaper 102 may be provided in the form of a pant-type diaper or may alternatively be provided with a re-closable fastening system, which may include fastener elements in various locations to help secure the diaper in position on the wearer. For example, fastener elements 148 may be located on the third and fourth ears 110, 112 and may be adapted to releasably connect with one or more corresponding fastening elements located in the first or second waist regions. It is to be appreciated that various types of fastening elements may be used with the diaper.

Figure 2A:
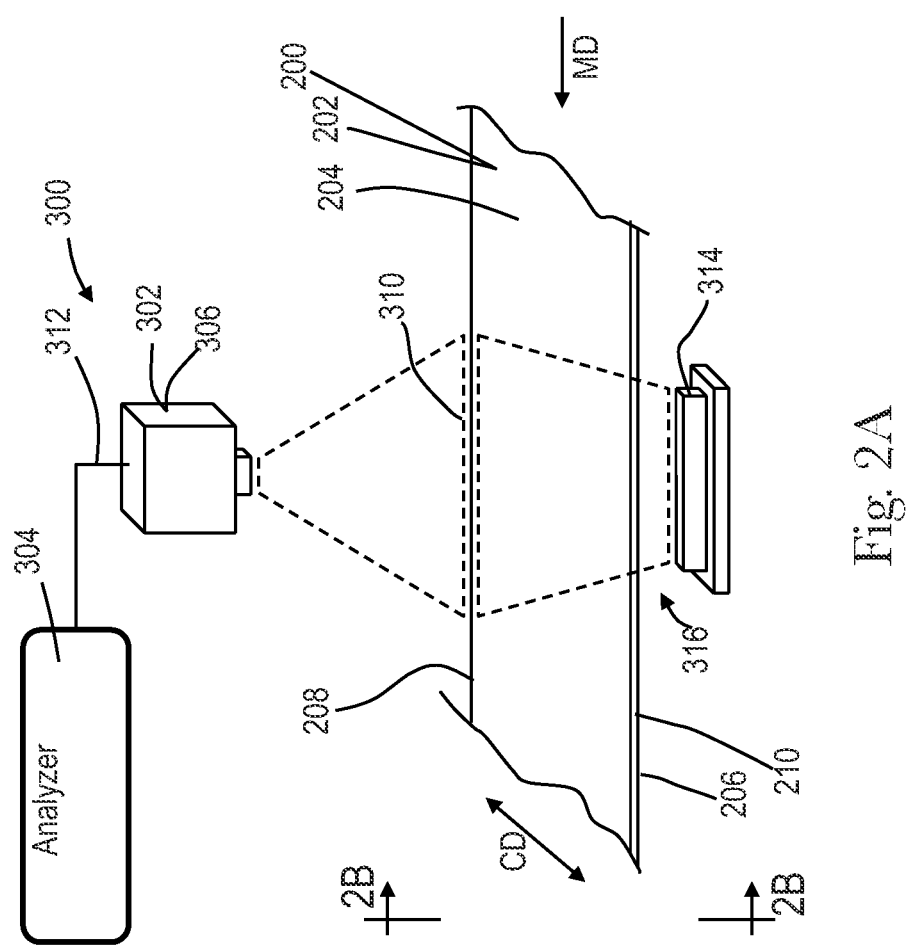
FIG. 2A is a schematic isometric view of an inspection system with a sensor adjacent an advancing substrate.

It is to be appreciated that the systems and methods disclosed herein are applicable to work with various types of converting processes and/or machines. For example, FIGS. 2A-2C show schematic representations of an absorbent article converting process including an inspection apparatus or system 300 for monitoring a substrate 200 advancing in a machine direction MD. The substrate 200 may be a continuous substrate 202 including a first surface 204 and an opposing second surface 206, and a first longitudinal side edge 208 and a second longitudinal side edge 210 separated from the first longitudinal side edge 208 in a cross direction CD. It is to be appreciated that the substrate 200 may be continuous or may be in the form of a discrete component 212, such as discussed below for example with reference to FIGS. 4A-4C and others. Thus, when in the form of discrete component 212, the substrate 200 may also include a first lateral side edge 214 and a second lateral side edge 216 separated from the first lateral side 214 edge to define a length in the machine direction. It is also to be appreciated that various substrates 200 can be used to construct various components of absorbent articles, such as backsheets, topsheets, ears, leg cuffs, elastic waist features, and absorbent cores. Exemplary descriptions of such absorbent article components are provided above with reference to FIG. 1.

Referring back to FIGS. 2A-2C, the inspection system 300 may be configured to interact with, monitor, and/or control a converting line. In some configurations, one or more sensors 302 may be arranged adjacent the converting line and/or the advancing substrate 200 and may communicate with an analyzer 304. Based on such communications, the analyzer 304 may monitor and affect various operations on the converting line. For example, the analyzer 304 may send various types of control commands to the converter line based on communications with the sensors 302. In some embodiments, the control commands may be in the form of reject commands communicated to a reject system. In some embodiments, the control commands may be in adapted the form commands to increase or decrease substrate advancement speeds and/or commands to reposition the substrate in cross direction CD.

For the purposes of the present discussion, the analyzer 304 is a field programmable gate array (FPGA), an application specific integrated circuit (ASIC), or a graphical processing unit (GPU). FPGA examples may include the National Instruments PCIe-1473R, National Instruments PXIe-1435, National Instruments 1483R with FLIXRIO FPGA module, Altera Stratix II, Altera Cyclone III, Xilinx Spartan 6, Xilink Vertex 6 or Vertex 7. GPU examples may include GeForce GTX 780 (Ti), Quadro K6000, Radeon R9 295X2 and Radeon HD 8990.

It is to be appreciated that the analyzer 304 may also be configured to communicate with one or more computer systems, such as for example, a programmable logic controller (PLC) and/or personal computer (PC) running software and adapted to communicate on an EthernetIP network. Some embodiments may utilize industrial programmable controllers such as the Siemens S7 series, Rockwell ControlLogix, SLC or PLC 5 series, or Mitsubishi Q series. The aforementioned embodiments may use a personal computer or server running a control algorithm such as Rockwell SoftLogix or National Instruments Labview or may be any other device capable of receiving inputs from sensors, performing calculations based on such inputs and generating control actions through servomotor controls, electrical actuators or electro-pneumatic, electrohydraulic, and other actuators. Process and product data may be stored directly in the aforementioned computer systems or may be located in a separate data historian. In some embodiments, the historian is a simple data table in the controller. In other embodiments, the historian may be a relational or simple database. Common historian applications include Rockwell Automation Factory Talk Historian, General Electric Proficy Historian, OSI PI, or any custom historian that may be configured from Oracle, SQL or any of a number of database applications. It is also to be appreciated that the analyzer 304 may be configured to communicate with various types of controllers and inspection sensors configured in various ways and with various algorithms to provide various types of data and perform various functions, for example, such as disclosed in U.S. Pat. Nos. 5,286,543; 5,359,525; 6,801,828; 6,820,022; 7,123,981; 8,145,343; 8,145,344; and 8,244,393; and European Patent No. EP 1 528 907 B1, all of which are incorporated by reference herein.

As shown in FIGS. 2A-2C and 3, the inspection system 300 includes an inspection sensor 302 configured as a line scan camera 306 having a linear array of pixel data 308 and defining a linear field of view 310. In addition, the line scan camera 306 is arranged relative the advancing substrate 200 such that the linear field of view 310 extends in the machine direction MD. It is to be appreciated that the linear array of pixel data 308 may be collected using an array of photodetectors. As such, it is to be appreciated that the line scan camera 306 may be any suitable camera with an array of pixel data 308 having significantly more pixels in one dimension than in the other. In some embodiments, the array 308 may be one-dimensional. As shown in FIG. 4, the array 308 may include various numbers of pixels, such as Pixel 1 through Pixel n. Example array sizes for line scan cameras may include, for example 1×1024 pixels and 1×2048 pixels. It is to be appreciated that the line scan camera 306 may include pixel arrays that are more than one pixel wide. As an example, a line scan camera 306 may have two pixels arranged in the cross direction CD, and may use a method of calculation such as averaging, binning, or summing to generate a single data point derived from those two pixels. It is also to be appreciated that the line scan camera 306 may be a focal plane array configured to utilize an array of adjacent or discontinuous pixels extending in the machine direction MD. Because of the one dimensional pixel array, the line scan camera 306 may have a roughly linear field of view 310 arranged to extend in the direction in which the substrate 200 is advancing, shown as the machine direction MD.

Examples of line-scan cameras 306 that may be used include, the Basler Runner; the Dalsa Spyder Series, such as the Dalsa Spyder 3 Gig E Vision Camera; the DVT 540LS smart camera; and the COGNEX 5604 smart camera. It is to be appreciated that different applications may utilize line scan cameras 306 that are sensitive in different frequency bands. For example, different line scan cameras 306 may be sensitive in the visible, ultra-violet and/or infrared range. Further, a line array sensor can also be considered a line scan camera, as described herein. For example, a Tichawa Contact Image Sensor could be used.

Figure 3A:
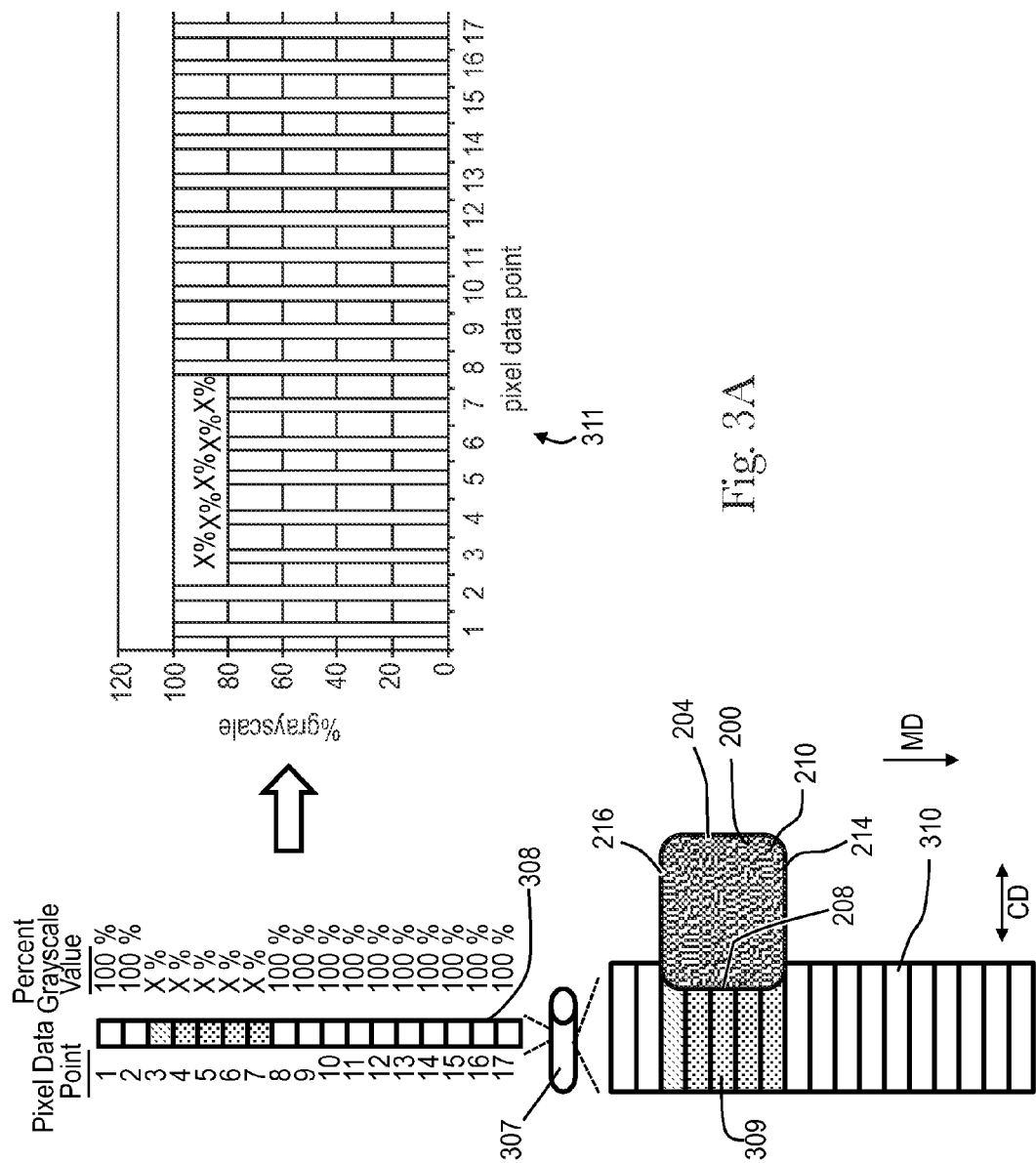
FIG. 3A is a first schematic block diagram showing an illustration of a cross direction CD position of a substrate correlated with percent grayscale values in a linear array of pixel data.
Figure 3B:
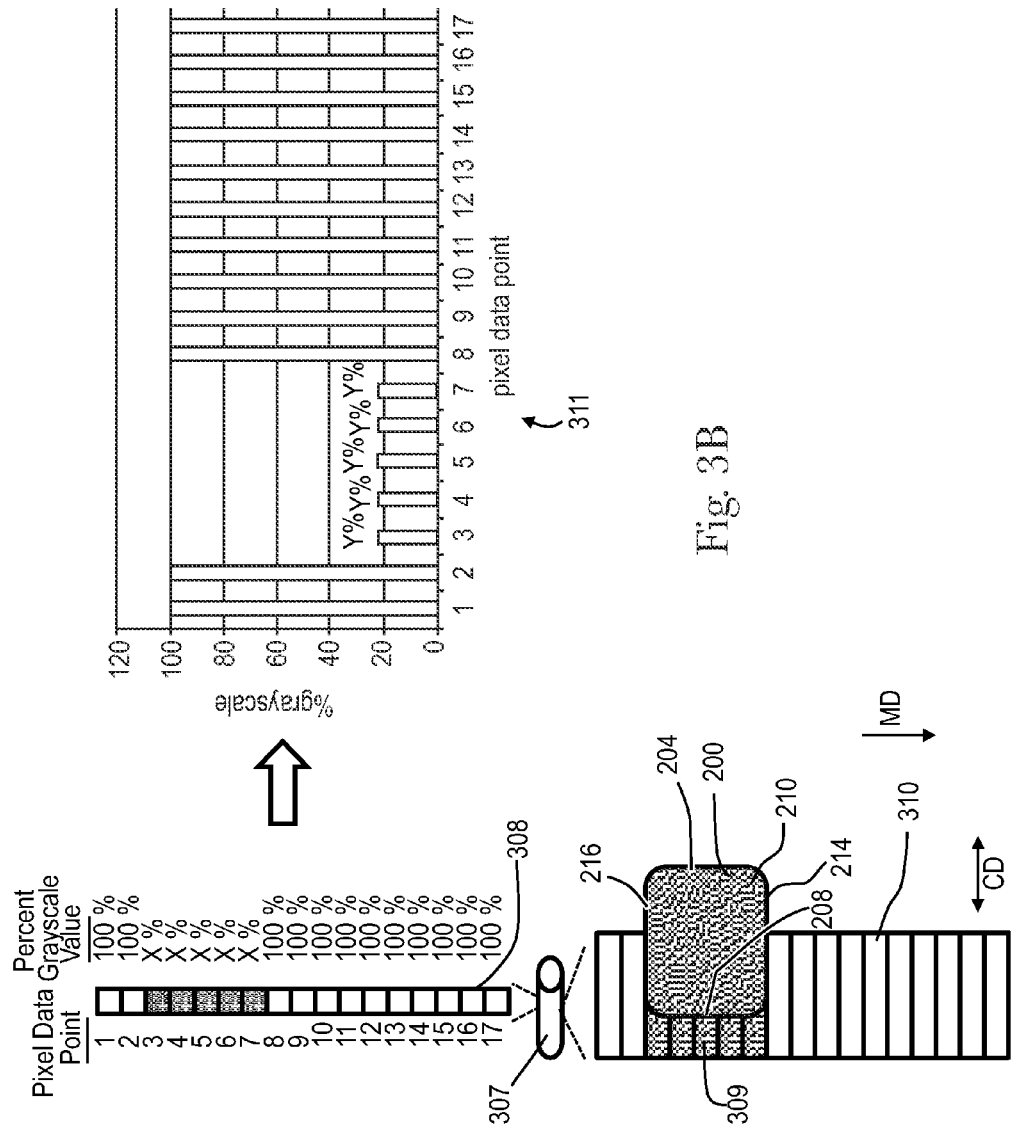
FIG. 3B is a second schematic block diagram showing an illustration of a cross direction CD position of a substrate correlated with percent grayscale values in a linear array of pixel data.
Figure 3C:
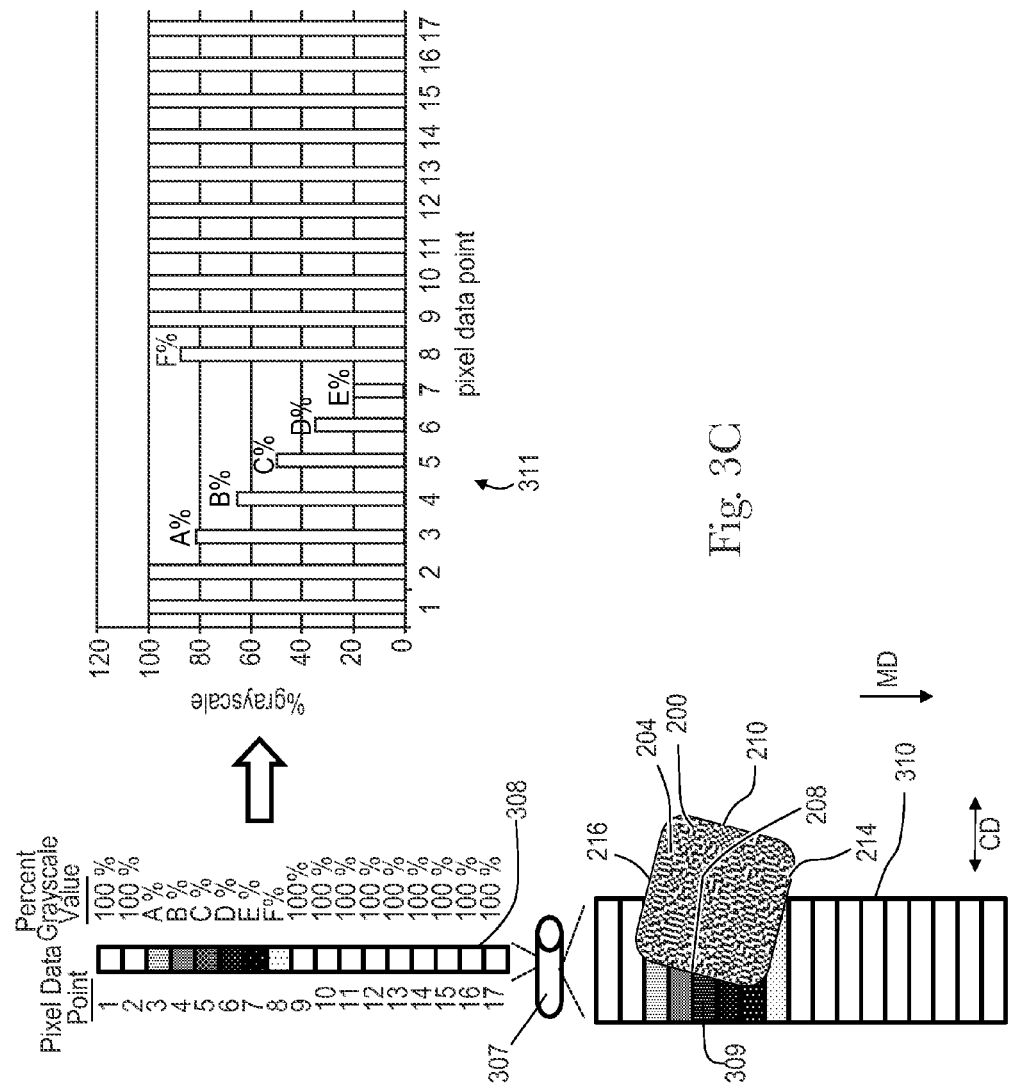
FIG. 3C is a third schematic block diagram showing an illustration of a cross direction CD position of a substrate correlated with percent grayscale values in a linear array of pixel data.
Figure 4:
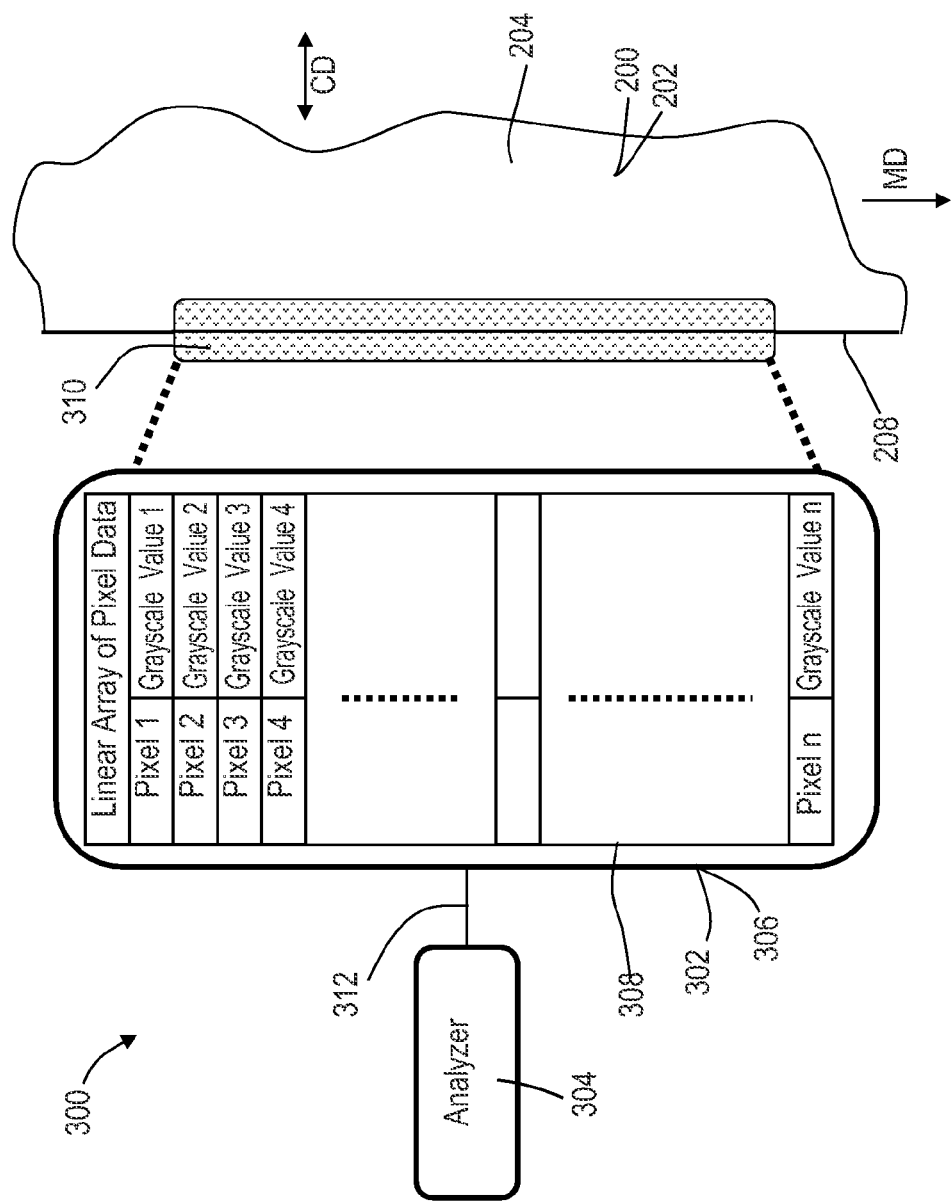
FIG. 4 is a detailed schematic top side view showing a longitudinal side edge of a continuous substrate advancing through a field of view of a line scan camera.
Figure 5A:
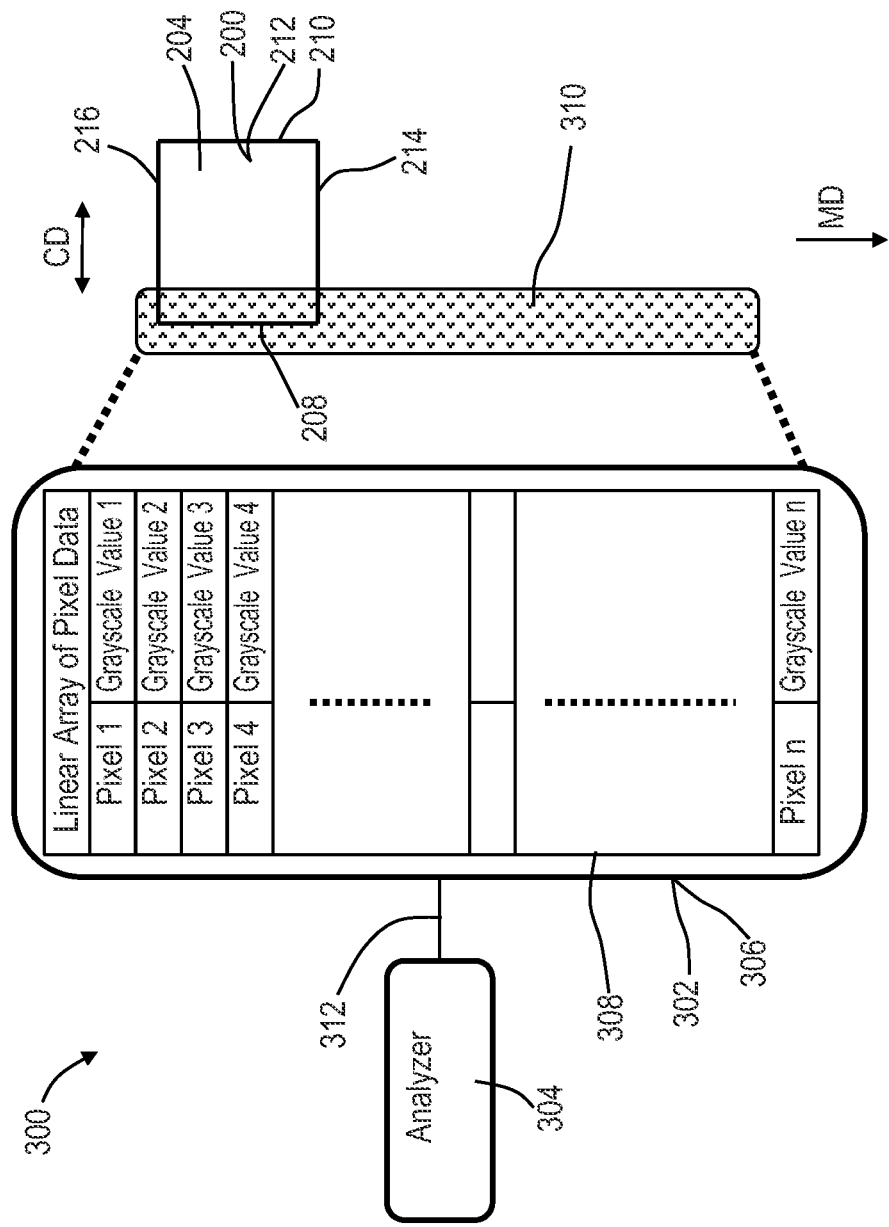
FIG. 5A is a detailed schematic top side view showing a longitudinal side edge and two lateral side edges of a substrate in the form of a discrete component advancing through a field of view of a line scan camera.
Figure 5B:
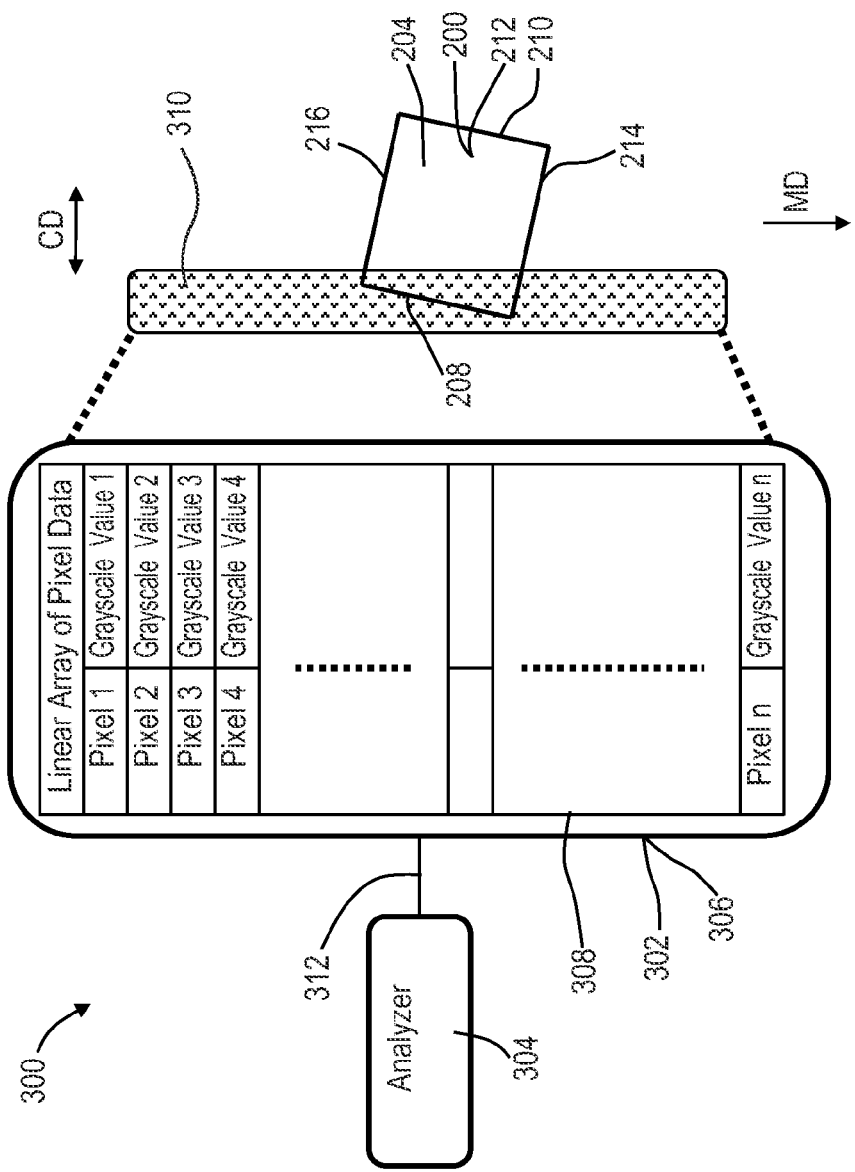
FIG. 5B is a detailed schematic top side view showing the continued advancement of the substrate from FIG. 5A through the field of view of the line scan camera.
Figure 5C:
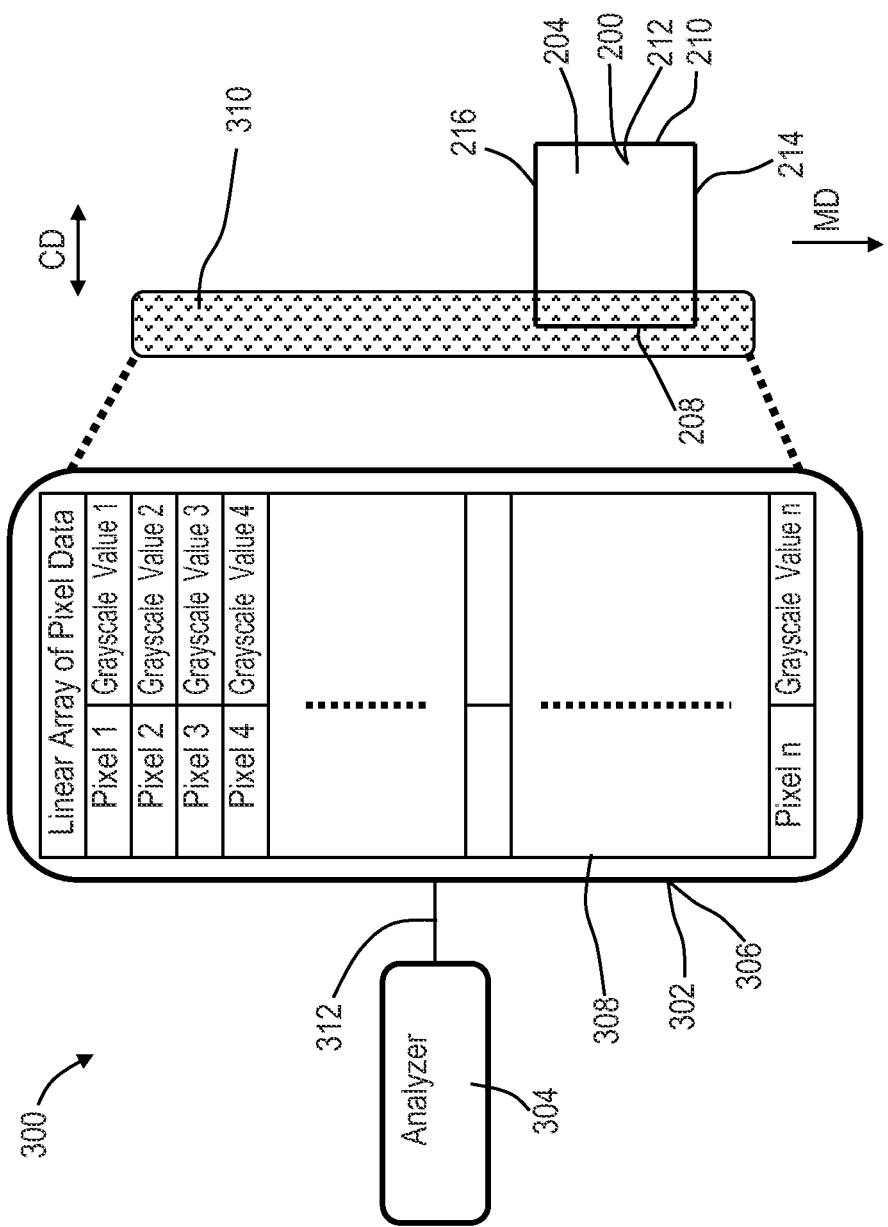
FIG. 5C is a detailed schematic top side view showing the continued advancement of the substrate from FIG. 5B through the field of view of the line scan camera.

It is to be appreciated that the field of view 310 of the line scan camera 306 may be determined by the size of the image array and by imaging optics 307, such as shown in FIGS. 3A-3C. As such, imaging optics may be selected to focus the field of view 310 onto the advancing substrate 200. Any suitable optical components may be used including, for example, lenses available from NAVITAR and SCHNEIDER OPTICS. In some configurations, the field of view 310 may be expanded by defocusing a lens associated with the line scan camera 306. In some configurations, the field of view 310 may be expanded by with the application of a spherical lens, cylindrical lens, and/or reflectors.

Referring back to FIGS. 2A-2C, the analyzer 304 may be in communication with the line scan camera 306 through a communication network 312. As such, it is to be appreciated that the analyzer 304 may be physically located the near the advancing substrate 200 and/or line scan camera 306 and/or may be located at another location and in communication with the line scan camera 306 via a wired and/or wireless network 312. In some embodiments, the communication network 312 is configured as a non-deterministic communication network, such as for example, Ethernet or Ethernet IP (industrial protocol) communication network.

With continued reference to FIGS. 2A-2C, the inspection apparatus or system 300 may also include an illumination source 314 configured to define an illumination field 316 that illuminates the linear field of view 310 and a portion of the advancing substrate 200. It is to be appreciated that the outer perimeter or contours of the illumination field 316 may or may not exactly correspond with the field of view 310. In some embodiments, the illumination field 316 may illuminate include areas of the advancing substrate outside of the field of view 310. In addition, it is to be appreciated that the inspection system 300 may be configured such that the illumination field 316 and the field of view 310 are located on the same surface of the advancing substrate 200 or located on opposing surfaces of the advancing substrate 200. For example, as shown in FIGS. 2A-2C, the illumination source 314 may be configured to backlight a portion of the substrate 200 advancing through the field of view 310. More particularly, the line scan camera 306 may be positioned adjacent the first surface 204 of the advancing substrate 200, and a portion of the first surface 204 may advance in the machine direction MD through the field of view 310. In addition, the illumination source 314 may be positioned adjacent the second surface 206 of the advancing substrate 200, and a portion of the second surface 206 of the substrate 200 may be illuminated while advancing through the illumination field 316. In other configurations, the illumination source 314 shown in FIGS. 2A-2C may be positioned adjacent the first surface 204 of the advancing substrate 200 along with the line scan camera 306. And as such, portion of the first surface 204 of the substrate 200 may be illuminated directly by the illumination source 314 while advancing through the illumination field 316 and the field of view 310.

It is to be appreciated that the illumination source 314 may be configured in various ways. For example, the illumination source 314 may comprise line lights such as light emitting diode (LED) line lights. Examples of such lights include the ADVANCED ILLUMINATION IL068, various line lights available from METAPHASE, various line lights available from VOLPI such as model number 60023, as well as various line lights available from CCS AMERICA, INC. In some embodiments, the illumination source 314 may include halogen or other source lights coupled to illuminate the field of view 316 with fiber bundles and/or panels. Other example illumination source 314 configurations may include halogen or other sources coupled to fiber bundles. For example, halogen sources may include those available from SCHOTT and fiber bundles and/or panels may include those available from SCHOTT and/or FIBEROPTICS TECHNOLOGY INC. In addition, the illumination source 314 may be configured to emit light in any suitable frequency range including, for example, ultra-violet, visible and/or infrared.

It is to be appreciated that configuring the system 300 to minimize the number of pixels and operations necessary may provide faster system responses. As such, it may be desirable to reconstruct the cross directional CD position and orientation of a longitudinal side edge 208, 210 of a substrate 200 using only a single data point along the cross direction CD. Thus, the CD position of a longitudinal side edge 208, 210 can be reconstructed by analyzing the grayscale magnitude of a single data point when the value of that point corresponds to the percentage of a region affected by the substrate 200 as compared to a background region 309. As previously mentioned, the field of view 310 may be expanded in the cross direction CD by defocusing a lens 307 associated with the line scan camera 306, such as shown in FIGS. 3A-3C. As such, data from a single pixel can be made to be representative of a relatively wide region in the cross direction CD due to the defocusing method. To illustrate the present methodology further, an example explanation of the utilizing grayscale magnitudes to reconstruct the cross directional CD position and orientation of a longitudinal side edge 208, 210 of a substrate 200 is provided below with reference to FIGS. 3A-3C.

FIG. 3A is a schematic block diagram showing an illustration of a cross direction CD position of a substrate 200 correlated with percent grayscale values in a linear array of pixel data 308 having 17 pixel data points, labeled 1-17. For the purposes of the present example illustration, it is assumed that the substrate 200 is relatively dark and the background 309 is relatively bright. Thus, as a relatively larger portion of the field of view 310 is obstructed by the substrate 200, the pixel array 308 senses a relatively lower grayscale value. Conversely, as a relatively smaller portion of the field of view 310 is obstructed by the substrate 200, the pixel array 308 senses a relatively higher grayscale value. As shown in FIG. 3A, the substrate 200 is partially covering regions of the field of view 310 corresponding with pixel data points 3-7, whereas the uncovered regions of the field of view 310 correspond with pixel data points 1, 2, and 8-17. As such, pixel data points 1, 2, and 8-17 may have a grayscale value of 100%. In turn, the pixel data points 3-7 may have a grayscale value of X %, wherein X is less than 100, as represented in the corresponding bar graph 311 shown in FIG. 3A.

Similar to FIG. 3A, FIG. 3B shows the substrate 200 as partially covering regions of the field of view 310 corresponding with pixel data points 3-7, whereas the uncovered regions of the field of view 310 correspond with pixel data points 1, 2, and 8-17. However, the substrate 200 shown in FIG. 3B shifted in the cross direction CD relative the field of view 310 and the substrate shown in FIG. 3A. As such, the substrate 200 in FIG. 3B is partially covering relatively larger regions of the field of view 310 corresponding with pixel data points 3-7, than as shown in FIG. 3A. Thus, in FIG. 3B, pixel data points 1, 2, and 8-17 may have a grayscale value of 100%. In turn, the pixel data points 3-7 may have a grayscale value of Y %, wherein Y is less than 100 and wherein Y is less than X, as represented in the corresponding bar graph 311 shown in FIG. 3B.

In yet another example similar to FIG. 3A, FIG. 3C shows the substrate 200 as partially covering regions of the field of view 310 corresponding with pixel data points 3-8, whereas the uncovered regions of the field of view 310 correspond with pixel data points 1, 2, and 9-17. However, the substrate 200 shown in FIG. 3C shifted and tilted in cross direction CD relative the field of view 310 and the substrate shown in FIG. 3A. As such, the substrate 200 in FIG. 3C is partially covering different sized regions of the field of view 310 corresponding with pixel data points 3-8, than as shown in FIG. 3A. Thus, in FIG. 3C, pixel data points 1, 2, and 9-17 may have a grayscale value of 100%. In turn, the pixel data points 3-8 may have a grayscale value of A %, B %, C %, D %, E %, and F %, respectively, wherein A, B, C, D, E, and F are all less than 100. In addition, the relative values of A, B, C, D, and E may be such that A>B>C>D>E as represented in the corresponding bar graph 311 shown in FIG. 3C. And F may also be greater than A, B, C, D, and E. Thus, the orientation of the substrate 200 with respect to the machine direction MD or cross direction CD can be determined by an analysis of a slope of the grayscale values.

With continued reference to FIGS. 3A-3C, to account for nonhomogeneous surface characteristics or opacities, binariztion of the data may be necessary as an initial step if the system cannot produce substantially clipped (0%) and saturated (100%) grayscale values corresponding to the substrate 200 and background 309, respectively. Due to the Gaussian distribution of the light power across the field of view 310, an inverse Gaussian function or look up table (LUT) may be required to linearize the pixel data to the position of the substrate 200. The corrected percent of grayscale range may be used to determine the position of the longitudinal side edge 208 within the field of view. Example corrected percent of grayscale ranges may be 0 to 65535 for a 16 bit sensor; 0 to 4095 for a 12 bit sensor; and 0 to 255 for an 8 bit sensor. It is to be appreciated that further analysis can be utilized to fit a known shape to the gradient of pixel data and determine the orientation of the longitudinal side edge of a substrate 200.

In the examples in FIGS. 3A-3C, the longitudinal edge 208 is illustrated as a straight line so a simple line fit can be used to determine the orientation. In configurations where the longitudinal side edge 208 defines a complex shape, a convolution or iterative LUT method may be utilized to fit the data and determine the orientation.

To provide additional context to the above discussion of the inspection system configuration of FIGS. 2A-2C and 3A-3C, the following provides a description of example implementations of the inspection systems and processes herein.

For example, FIG. 4 is a detailed view of a continuous substrate 202 showing portions of the first surface 204 and the first longitudinal side edge 208 advancing in the machine direction MD though the linear field of view 310 of the line scan camera 306. As such, the line scan camera 306 communicates sets of grayscale values of pixels from the linear array of pixel data 308 to the analyzer 304. In turn, the analyzer may be configured to determine various information about the advancing substrate 200 based on the grayscale value of at least one pixel, such as for example, a position of the first longitudinal edge 208 and/or velocity of the advancing substrate 200.

In one example, with configured reference to FIG. 4, as the substrate 200, 202 advances in the machine direction MD, the line scan camera 306 may communicate a first set of grayscale values of pixels from the linear array of pixel data 308 to the analyzer 304. And as such, the analyzer may determine a first position of the first longitudinal side edge 208 based on the grayscale value of at least one pixel. In some configurations, the first position of the first longitudinal side edge 208 may correspond with an angular orientation of the first longitudinal side edge 208 relative to the machine direction MD. In some configurations, the first position of the first longitudinal side edge 208 may correspond with a cross direction CD location relative to a fixed location. In turn, the analyzer 304 may be configured compare the first position of the first longitudinal side edge 208 with a target position. In some configurations, the analyzer 304 may also be configured to control various unit operations to reposition the first longitudinal side edge 208 subsequent to determining the first position of the first longitudinal side edge 208. As such, the analyzer 304 may be configured to communicate control commands reposition the first longitudinal side edge 208 by changing an angular orientation of the first longitudinal side edge 208 of relative to the machine direction MD. In some configurations, the analyzer 304 may be configured to communicate control commands reposition the first longitudinal side edge 208 by moving the substrate 208 in the cross direction CD.

With continued reference to FIGS. 2A-2C and 3, as the as the substrate 200 continues to advance in the machine direction MD, the line scan camera 306 may communicate a second set of grayscale values of pixels from the linear array of pixel data 308 to the analyzer 304. And as such, the analyzer 304 may determine a second position of the first longitudinal side edge 208 based on the grayscale value of at least one pixel. In some configurations, the analyzer 304 may also calculate a velocity of the substrate 202 based on the first position and the second position.

In another example, FIGS. 4A-4C show detailed views of a substrate 200 in the form of a discrete component 212 and showing portions of the first surface 204, the first longitudinal side edge 208, the first lateral side edge 214, and the second lateral side edge 216 advancing in the machine direction MD though the linear field of view 310 of the line scan camera 306. The substrate is oriented such that the first lateral side edge 214 is a leading edge, and the second lateral side edge 216 is a trailing edge. In a manner similar to the above discussion, the line scan camera 306 communicates sets of grayscale values of pixels from the linear array of pixel data 308 to the analyzer 304. In turn, the analyzer may be configured to determine various information about the advancing substrate 200 based on the grayscale value of at least one pixel, such as for example, positions of the first longitudinal edge 208 and/or lateral side edges 214, 216, and/or velocity of the advancing substrate 212. It is to be appreciate that the configuration shown in FIGS. 4A-4C may be modified such that the first lateral side edge 214 and the second lateral side edge 216 advance in the machine direction MD though the linear field of view 310 of the line scan camera 306, whereas the first longitudinal side edge 208 does not advance through the linear field of view 310.

With continued reference to FIG. 4A, the substrate 200, 202 may advance in the machine direction MD, and the line scan camera 306 may communicate a first set of grayscale values of pixels from the linear array of pixel data 308 to the analyzer 304. And as such, the analyzer may determine a first position of the first longitudinal side edge 208 and/or lateral side edges 214, 216 based on the grayscale value of at least one pixel. In some configurations, the first position of the first longitudinal side edge 208 and/or lateral side edges 214, 216 may correspond with an angular orientation of the first longitudinal side edge 208 and/or lateral side edges 214, 216 relative to the machine direction MD. In some configurations, the first position of the first longitudinal side edge 208 and/or lateral side edges 214, 216 may correspond with a cross direction CD location relative to a fixed location.

FIG. 4B shows continued advancement of the substrate 200, 212 in the machine direction MD from FIG. 4A. As shown in FIG. 4B, the substrate 200 is oriented slightly different with respect to the machine direction MD and cross direction CD as is illustrated in FIG. 4A. Thus, in FIG. 4B, the line scan camera 306 may communicate a second set of grayscale values of pixels from the linear array of pixel data 308 to the analyzer 304. And as such, the analyzer 304 may determine a second position of the first longitudinal side edge 208 and/or lateral side edges 214, 216 based on the grayscale value of at least one pixel. In turn, the analyzer 304 may be configured compare the second position of the first longitudinal side edge 208 and/or lateral side edges 214, 216 with a target position. As previously mentioned, the analyzer 304 may also be configured to control various unit operations to reposition the first longitudinal side edge 208 and/or lateral side edges 214, 216 subsequent to determining the second position of the first longitudinal side edge 208 and/or lateral side edges 214, 216. As such, the analyzer 304 may be configured to communicate control commands reposition the first longitudinal side edge 208 and/or lateral side edges 214, 216 by changing an angular orientation of the first longitudinal side edge 208 and/or lateral side edges 214, 216 relative to the machine direction MD or cross direction CD. In some configurations, the analyzer 304 may be configured to communicate control commands reposition the first longitudinal side edge 208 and/or lateral side edges 214, 216 by moving the substrate 212 in the cross direction CD. For example, FIG. 4C shows continued advancement of the substrate 200, 212 in the machine direction MD from FIG. 4B after the orientation of the orientation of the substrate 212 with respect to the machine direction MD and cross direction CD has been returned to substantially the same orientation as shown in FIG. 4A.

Although the substrates 200 illustrated in the attached figures having substantially straight longitudinal side edges 208, 210 and lateral side edges 214, 216, it is to be appreciated that the substrate 200 may have various shapes and sizes other than what are illustrated. For example, the substrate 200 whether in the form of a continuous substrate 202 or a discrete component 212, may include curved and/or non parallel longitudinal side edges 208, 210 having the same or different lengths. In addition, the substrate 200 in the form of a discrete component 212 may include curved and/or non parallel lateral side edges 214, 216 having the same or different lengths.

Figure 6A:
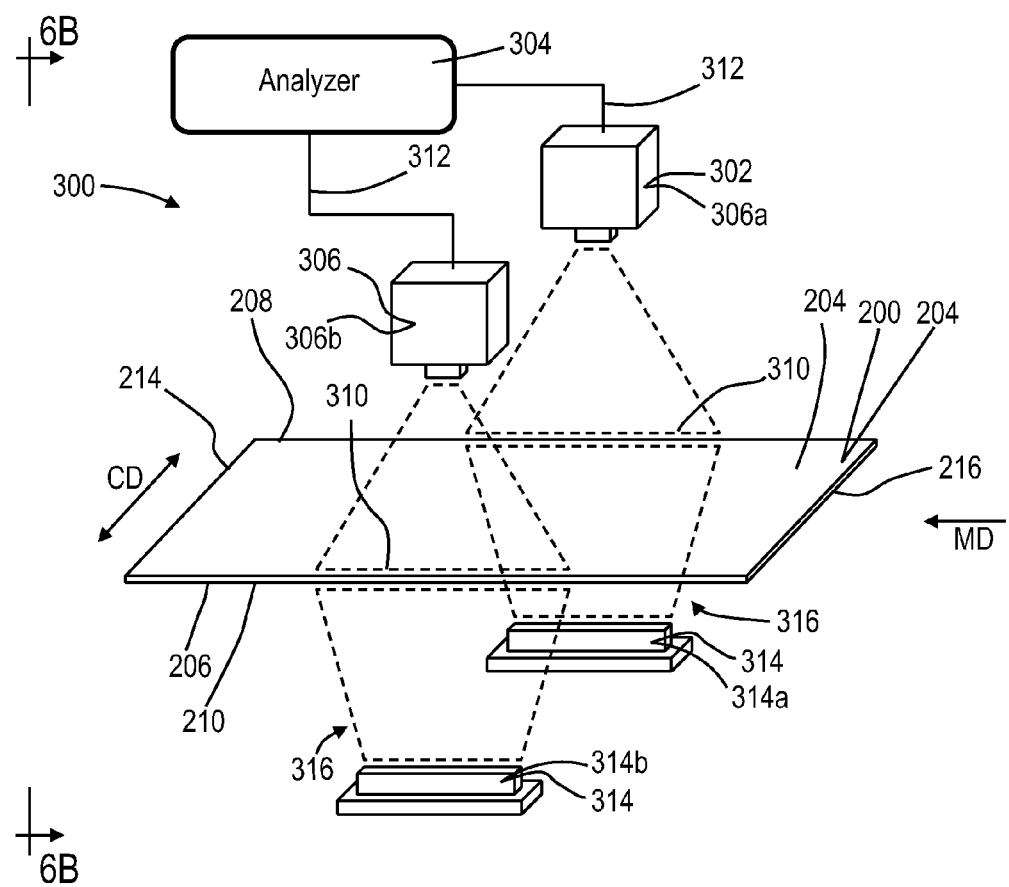
FIG. 6A is a schematic isometric view of an inspection system with two sensors adjacent an advancing substrate.
Figure 6B:
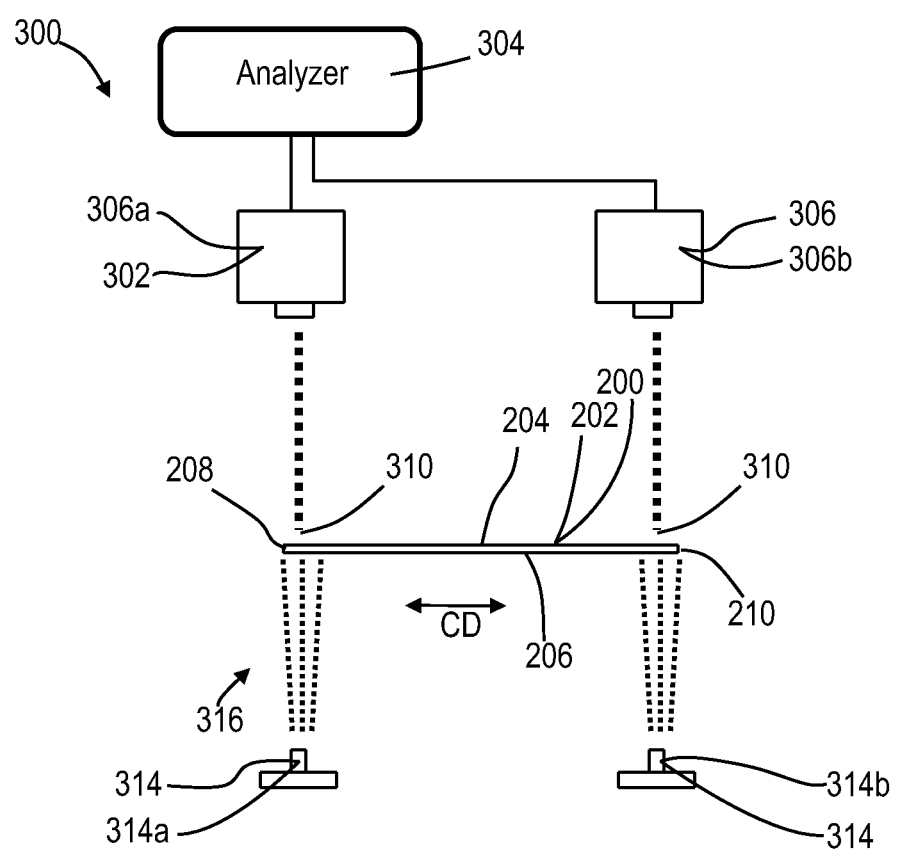
FIG. 6B is a side view of the inspection system and advancing substrate taken along the sectional line 6B-6B of FIG. 6A.

As previously mentioned, the inspection system 300 may configured in various ways and include more than one analyzer 304, line scan camera 306, and/or illumination source 314. For example, FIGS. 6A and 6B show the inspection system 300 configured with a first line scan camera 306a and a second line scan camera 306b. Each line scan camera 306a, 306b includes a linear array of pixel data 308 and defines a linear field of view 310. In some embodiments, a plurality of line scan cameras 306 may be derived by configuring focal plane arrays to utilize a substantially linear subset of pixels for each field of view 310. In addition, the line scan cameras 306a, 306b are arranged relative the advancing substrate 200 such that each linear field of view 310 extends in the machine direction MD as discussed above with reference to FIGS. 2A-2C. The inspection apparatus or system 300 shown in FIGS. 6A and 6B may also include a first illumination source 314a and a second illumination source 314b. The first illumination source 314a may be configured to define an illumination field 316 that illuminates the linear field of view 310 of the first line scan camera 306a as well as a portion of the advancing substrate 200. And the second illumination source 314a may be configured to define an illumination field 316 that illuminates the linear field of view 310 of the second line scan camera 306b as well as a portion of the advancing substrate 200.

Figure 7A:
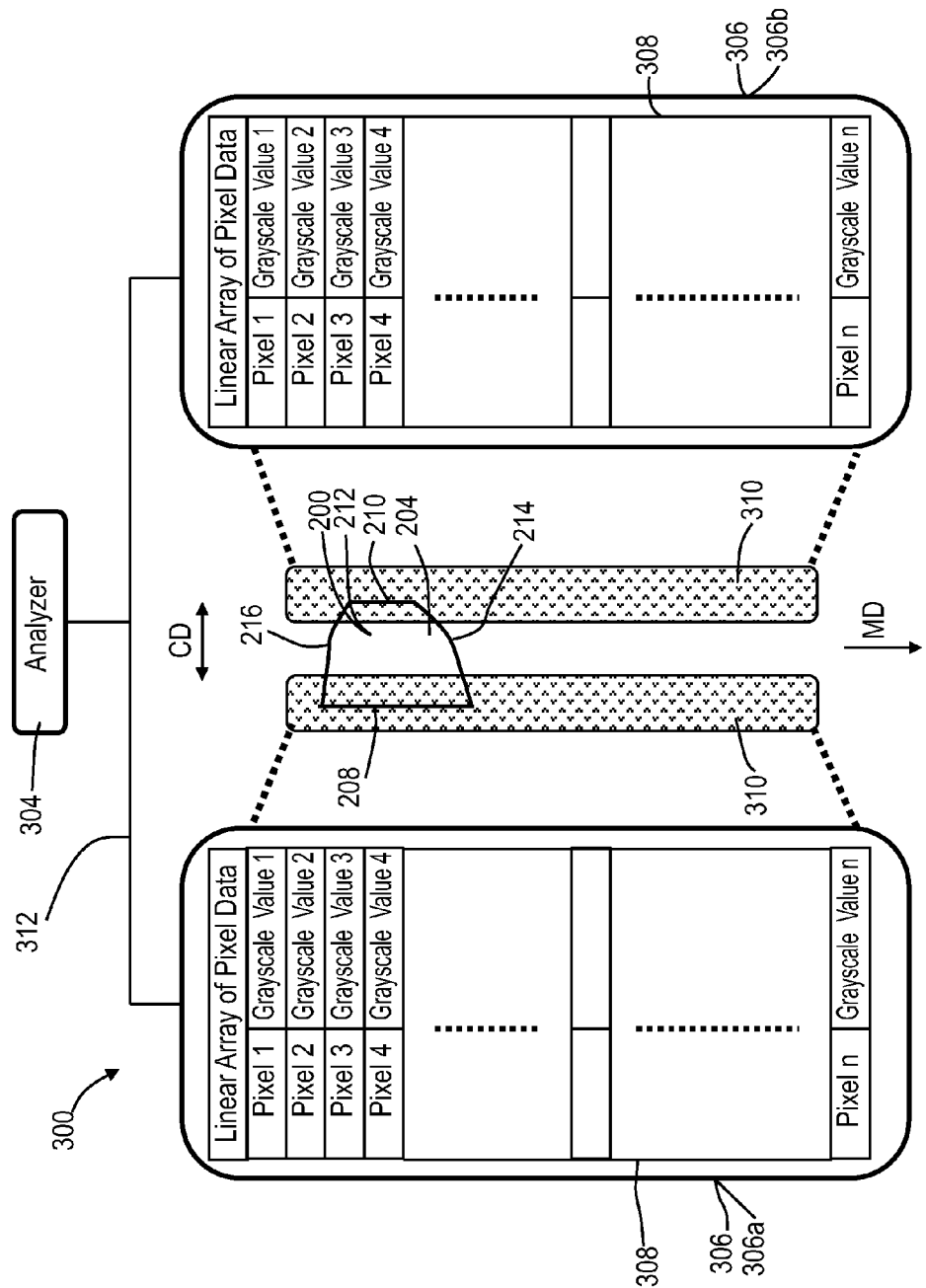
FIG. 7A is a detailed schematic top side view showing two longitudinal side edges and two lateral side edges of a substrate in the form of a discrete component advancing through fields of view of two line scan cameras.

It is to be appreciated that the inspection system 300 configuration shown in FIGS. 6A and 6B may be adapted to operate in various ways. For example, FIGS. 7A-7C show detailed views of an advancing substrate 200 in the form of a discrete component 212 and associated first surface 204, the first longitudinal side edge 208, the first lateral side edge 214, and the second lateral side edge 216. As shown in FIG. 6A, portions of the first surface 204, the first longitudinal side edge 208, the first lateral side edge 214, and the second lateral side edge 216 are advancing in the machine direction MD though the linear field of view 310 of the first line scan camera 306a. And portions of the first surface 204, the second longitudinal side edge 210, the first lateral side edge 214, and the second lateral side edge 216 are advancing in the machine direction MD though the linear field of view 310 of the second line scan camera 306b. The substrate is oriented such that the first lateral side edge 214 is a leading edge, and the second lateral side edge 216 is a trailing edge.

In a manner similar to the above discussion, each line scan camera 306a, 306b may communicate sets of grayscale values of pixels from the linear array of pixel data 308 to the analyzer 304. In turn, the analyzer 304 may be configured to determine various information about the advancing substrate 200 based on the grayscale value of at least one pixel, such as for example, positions of the longitudinal side edge 208, 210 and/or lateral side edges 214, 216, and/or velocity of the advancing substrate 212. It is to be appreciate that the configuration shown in FIGS. 7A-7C may be modified such that the first lateral side edge 214 and the second lateral side edge 216 advance in the machine direction MD though the linear field of view 310 of the first line scan camera 306a, whereas the first longitudinal side edge 208 does not advance through the linear field of view 310 of the first line scan camera 306a. And the first lateral side edge 214 and the second lateral side edge 216 may advance in the machine direction MD though the linear field of view 310 of the second line scan camera 306b, whereas the second longitudinal side edge 210 does not advance through the linear field of view 310 of the second line scan camera 306b.

With continued reference to FIG. 7A, the substrate 200, 212 may advance in the machine direction MD, and the first line scan camera 306a may communicate a first set of grayscale values of pixels from the linear array of pixel data 308 to the analyzer 304. In addition, the second line scan camera 306b may communicate a first set of grayscale values of pixels from the linear array of pixel data 308 to the analyzer 304. And as such, the analyzer may determine a first position of the longitudinal side edges 208, 210 and/or lateral side edges 214, 216 based on the grayscale value of at least one pixel. In some configurations, the first position of the longitudinal side edges 208, 210 and/or lateral side edges 214, 216 may correspond with an angular orientation of the longitudinal side edges 208, 210 and/or lateral side edges 214, 216 relative to the machine direction MD or cross direction CD. In some configurations, the first position of the longitudinal side edges 208, 210 and/or lateral side edges 214, 216 may correspond with a cross direction CD location relative to a fixed location.

FIG. 7B shows continued advancement of the substrate 200, 212 in the machine direction MD from FIG. 7A. As shown in FIG. 7B, the substrate 200 is oriented slightly different with respect to the machine direction MD and cross direction CD as is illustrated in FIG. 7A. Thus, in FIG. 7B, each line scan camera 306a, 306b may communicate a second set of grayscale values of pixels from the linear array of pixel data 308 to the analyzer 304. And as such, the analyzer 304 may determine a second position of the longitudinal side edges 208, 210 and/or lateral side edges 214, 216 based on the grayscale value of at least one pixel. In turn, the analyzer 304 may be configured compare the second position of the longitudinal side edges 208, 210 and/or lateral side edges 214, 216 with a target position. As previously mentioned, the analyzer 304 may also be configured to control various unit operations to reposition the longitudinal side edges 208, 210 and/or lateral side edges 214, 216 subsequent to determining the second position of the longitudinal side edges 208, 210 and/or lateral side edges 214, 216. As such, the analyzer 304 may be configured to communicate control commands reposition the longitudinal side edges 208, 210 and/or lateral side edges 214, 216 by changing an angular orientation of the longitudinal side edges 208, 210 and/or lateral side edges 214, 216 relative to the machine direction MD or cross direction CD. In some configurations, the analyzer 304 may be configured to communicate control commands reposition the longitudinal side edges 208, 210 and/or lateral side edges 214, 216 by moving the substrate 212 in the cross direction CD. For example, FIG. 7C shows continued advancement of the substrate 200, 212 in the machine direction MD from FIG. 7B after the orientation of the orientation of the substrate 212 with respect to the machine direction MD and cross direction CD has been returned to substantially the same orientation as shown in FIG. 7A.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method for manufacturing an absorbent article, the method comprising the steps of:
providing a line scan camera comprising a linear array of pixel data and defining a linear field of view;
providing an analyzer selected from the group consisting of: a field programmable gate array, an application specific integrated circuit, and graphical processing unit;
arranging the line scan camera such that the linear field of view extends in a machine direction;
operating an illumination source to define an illumination field that illuminates the linear field of view;
providing a substrate comprising a first surface and an opposing second surface, the substrate further comprising a first longitudinal side edge and a second longitudinal side edge separated from the first longitudinal side edge in a cross direction;
advancing the substrate in the machine direction such that the first longitudinal side edge travels through the linear field of view;
communicating a first set of grayscale values of pixels from the linear array of pixel data from the line scan camera to the analyzer; and
determining a first position of the first longitudinal side edge based on the grayscale value of at least one pixel.

2. The method of claim 1, further comprising the step of expanding the linear field of view in the cross direction with a cylindrical lens.

3. The method of claim 1, wherein the linear array of pixel data is collected using an array of photodetectors.

4. The method of claim 1, wherein the step of advancing the substrate in the machine direction further comprises advancing a portion of the first surface through the linear field of view.

5. The method of claim 4, wherein the step of operating the illumination source further comprises illuminating a portion of the first surface.

6. The method of claim 4, wherein the step of operating the illumination source further comprises illuminating a portion of the second surface.

7. The method of claim 1, wherein the first position of the first longitudinal side edge corresponds with an angular orientation of the first longitudinal side edge relative to the machine direction.

8. The method of claim 1, wherein the first position of the first longitudinal side edge corresponds with a cross direction location relative to a fixed location.

9. The method of claim 1, further comprising the step of comparing the first position of the first longitudinal side edge with a target position.

10. The method of claim 1, further comprising the step of repositioning the first longitudinal side edge subsequent to determining the first position of the first longitudinal side edge.

11. The method of claim 10, wherein the step of repositioning the first longitudinal side edge further comprises changing an angular orientation of the first longitudinal side edge of relative to the machine direction.

12. The method of claim 10, wherein the step of repositioning the first longitudinal side edge further comprises moving the substrate in the cross direction.

13. The method of claim 10, further comprising the steps of:
communicating a second set of grayscale values of pixels from the linear array of pixel data from the line scan camera to the analyzer; and
determining a second position of the first longitudinal side edge based on the grayscale value of at least one pixel.

14. The method of claim 13, further comprising the step of calculating a velocity of the substrate based on the first position and the second position.

15. The method of claim 1, wherein the substrate further comprises a discrete component comprising a first lateral side edge and a second lateral side edge.

16. The method of claim 15, further comprising the step of determining a first position of the first lateral side edge based on the grayscale value of at least one pixel.

17. The method of claim 15, wherein the first lateral side edge comprises a leading edge and wherein the second lateral side edge comprises a trailing edge.

18. A method for manufacturing an absorbent article, the method comprising the steps of:
providing a first line scan camera comprising a linear array of pixel data and defining a first linear field of view;
providing a second line scan camera comprising a linear array of pixel data and defining a second linear field of view;
providing an analyzer selected from the group consisting of: a field programmable gate array, an application specific integrated circuit, and graphical processing unit;
arranging the first and second line scan cameras such that the first and second linear fields of view extend in a machine direction;
operating an illumination source to define an illumination field that illuminates the first and second linear fields of view;
providing a substrate comprising a discrete component having a width in the cross direction, the substrate further comprising a first lateral side edge and a second lateral side edge separated from the first lateral side edge to define a length in the machine direction;
advancing the substrate in the machine direction such that the first and second lateral side edges travel through the first linear field of view, and such that the first and second lateral side edges travel through the second linear field of view;
communicating a first set of grayscale values of pixels from the linear array of pixel data from the first and second line scan cameras to the analyzer; and
communicating a second set of grayscale values of pixels from the linear array of pixel data from the first and second line scan cameras to the analyzer; and
determining an orientation of the substrate relative to the machine direction based on the first and second sets of grayscale values of at least two pixels.

19. The method of claim 18, further comprising the step of expanding the first linear field of view in the cross direction with a cylindrical lens.

20. The method of claim 18, wherein the linear arrays of pixel data are collected using an array of photodetectors.

21. An apparatus for monitoring a substrate advancing along a converting apparatus in a machine direction, the substrate comprising a first surface and an opposing second surface, the substrate further comprising a first longitudinal side edge and a second longitudinal side edge separated from the first longitudinal side edge to define a width in a cross direction, the apparatus comprising:
a communication network;
an analyzer connected with the communication network, the analyzer comprising a linear array of pixel data and defining a linear field of view extending in the machine direction, wherein the analyzer is selected from the group consisting of: a field programmable gate array, an application specific integrated circuit, and graphical processing unit;
a line scan camera connected with the communication network, the line scan camera comprising a linear array of pixel data and defining a linear field of view, wherein the line scan camera is arranged such that the linear field of view extends in the machine direction;
an illumination source defining an illumination field that illuminates the linear field of view; and
wherein the analyzer is configured to determine a position of the first longitudinal side edge of the substrate based on based on a set of grayscale values of pixels from the linear array of pixel data from the analyzer.

22. The apparatus of claim 21, further comprising a cylindrical lens adapted to expand the linear field of view in a cross direction.

23. The apparatus of claim 21, wherein the line scan camera comprises a focal plane array.

* * * * *